United States Patent [19]

Woo

[11] Patent Number: 4,701,319

[45] Date of Patent: Oct. 20, 1987

[54] TOOTHPASTE COMPOSITIONS

[75] Inventor: Ricky A. Woo, Cincinnati, Ohio

[73] Assignee: The Procter & Gamble Company, Cincinnati, Ohio

[21] Appl. No.: 650,757

[22] Filed: Sep. 14, 1984

[51] Int. Cl.⁴ .............................. A61K 7/16; A61K 7/18
[52] U.S. Cl. ............................................. 424/52; 424/49
[58] Field of Search ...................................... 424/49–58

[56] References Cited

U.S. PATENT DOCUMENTS

| | | | |
|---|---|---|---|
| 3,194,738 | 7/1965 | Harrison et al. | 167/93 |
| 3,927,202 | 12/1975 | Harvey et al. | 424/57 |
| 3,944,661 | 3/1976 | Colodney et al. | 424/49 |
| 4,020,154 | 4/1977 | Perla et al. | 424/49 |
| 4,071,614 | 1/1978 | Grimm, III | 424/49 |
| 4,071,615 | 1/1978 | Barth | 424/52 |
| 4,132,771 | 1/1979 | Schreiber et al. | 424/52 |
| 4,150,106 | 4/1979 | Assal et al. | 424/7 |
| 4,254,101 | 3/1981 | Denny, Jr. | 424/52 |
| 4,256,730 | 3/1981 | Benedict | 424/52 |
| 4,344,931 | 8/1982 | Aguilar | 424/52 |
| 4,353,890 | 10/1982 | Scott | 424/49 |

Primary Examiner—Shep K. Rose
Attorney, Agent, or Firm—Richard C. Witte; John V. Gorman; Douglas C. Mohl

[57] ABSTRACT

Toothpastes are disclosed which contain water, humectant, a dentifrice abrasive, a carboxyvinyl polymer and carrageenan.

10 Claims, No Drawings

TOOTHPASTE COMPOSITIONS

TECHNICAL FIELD

The present invention relates to toothpaste compositions possessing good phase separation stability, good vicosity and favorable processing properties. If the product contains fluoride, good fluoride stability is also achieved.

Achieving toothpastes which possess these properties is not without certain difficulties. For example binders react differently depending on the amount of water, humectant and other materials present. Therefore it is not always possible to predict what properties a paste will possess. The present inventor has found that certain combinations of a carboxyvinyl polymer and a carrageenan provide a paste with the properties described above.

With toothpaste which contain fluoride, concerns are also present around the availability of the fluoride ion. It has been postulated that the effectiveness of fluoride toothpastes in providing enamel antisolubility benefits is dependent upon the amount of fluoride ion which is available for uptake by the enamel being treated. It is, of course, therefore desirable to formulate toothpaste products which provide maximum fluoride ion availability in brushing solutions formed therefrom.

BACKGROUND ART

The prior art discloses the binders of the present invention in a variety of toothpaste compositions but not combined in the manner of the present invention. Included among such references are U.S. Pat. No. 3,980,767, Sept. 14, 1976 to Chown et al; U.S. Pat. No. 3,919,409, Nov. 11, 1975 to Perla et al; U.S. Pat. No. 3,911,904, Oct. 7, 1975 to Harrison; U.S. Pat. No. 3,711,604, Jan. 16, 1973 to Colodney et al; and U.S. Pat. No. 3,935,306, Jan. 27, 1976 to Roberts et al.

Additional references include U.S. Pat. No. 4,150,106, Apr. 17, 1979 to Assal et al; U.S. Pat. No. 4,353,890, Oct. 12, 1982 to Scott; and U.S. Pat. No. 4,254,101, Mar. 3, 1981 to W. D. Denny. The Assal et al reference discloses mixtures of a carboxyvinyl polymer and a carrageenan but not in compositions of the type claimed herein.

It is an object of the present invention to provide toothpastes having improved consistency, stand up and handling characteristics.

It is a further object of the present invention to provide toothpastes which have quick viscosity buildup and improved stability.

It is still a further object of this invention to provide toothpastes having excellent fluoride stability.

These and other objects will becomes readily apparent from the detailed description which follows.

All percentages and ratios uses herein are by weight unless otherwise specified.

DISCLOSURE OF THE INVENTION

The present invention relates to toothpaste compositions which exhibit excellent stability, viscosity and processing properties. In addition, the compositions can be formulated to provide excellent fluoride stability. Such compositions comprise a dental abrasive, a carboxyvinyl polymer, carrageenan, a humectant and water.

The amounts of the components in the compositions are as follows:
from about 6% to about 35% of a dental abrasive;
from about 0.01% to about 0.8% of a carboxyvinyl polymer;
from about 0.10% to about 1.7% of an iota form carrageenan;
from about 20% to about 70% of a humectant; and
q.s. 100% water.

The compositions have a pH in the range of from about 6 to about 8. The compositions may be in the form of clear or translucent gels or opaque pastes.

DETAILED DESCRIPTION OF THE INVENTION

The essential as well as optional components of the present compositions are discussed in detailed below:

DENTAL ABRASIVE

The abrasive polishing material contemplated for use in the present invention can be any material which does not excessively abrade dentin. These include, for example, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and other such as disclosed by Cooley et al in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein.

The silica abrasive polishing materials useful herein, as well as the other abrasives, generally have an average particle size ranging between about 0.1 to 30 microns, preferably 5 and 15 microns. The silica abrasive can be precipitated silica or silica gels such as the silica xerogels described in Pader et al, U.S. Pat. No. 3,538,230, issued Mar. 2, 1970 and DiGiulio, U.S. Pat. No. 3,862,307, June 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, July 29, 1982, incorporated herein by reference.

The abrasive in the compositions described herein is present at a level of from about 6% to about 35%, preferably from about 15% to about 25%.

CARBOXYVINYL POLYMER

The term "carboxyvinyl polymer" as used herein describes a family of compounds disclosed and claimed in U.S. Pat. No. 2,798,053 issued on July 2, 1957, to Brown, the specification of which is hereby incorporated by reference. Methods for making carboxyvinyl polymers are also disclosed in Brown.

A carboxyvinyl polymer is an interpolymer of a monomeric mixture comprising a monometric olefinically unsaturated carboxylic acid, and from about 0.1% to about 10% by weight of the total monomers of polyether of a polyhydric alcohol, which polyhydric alcohol contains at least four carbon atoms to which are attached at least three hydroxyl groups, the polyether containing more than one alkenyl group per molecule. Other monoolefinic monomeric materials may be present in the monomeric mixture if desired, even in predominant proportion. Carboxyvinyl polymers are substantially insoluble in liquid, volatile organic hydrocarbons and is dimensionally stable on exposure to air.

Preferred polyhydric alcohols used to produce carboxyvinyl polymers include polyols selected from the class consisting of oligosaccharides, reduced derivatives thereof in which the carbonyl group is converted to an alcohol group, and pentaerythritol; more preferred are oligosaccharides; most preferred is sucrose. It is preferred that the hydroxyl groups of the polyol which are modified be etherified with ally groups, the polyol having at least two allyl ether groups per polyol molecule. When the polyol is sucrose, it is preferred that the sucrose have at least about five allyl ether groups per sucrose molecule. It is preferred that the polyether of the polyol comprise from about 0.1% to about 4% of the total monomers, more preferably from about 0.2% to about 2.5%.

Preferred monomeric olefinically unsaturated carboxylic acids for use in producing carboxyvinyl polymers used herein include monomeric, polymerizable, alpha-beta monoolefinically unsaturated lower aliphatic carboxylic acids; more preferred are monomeric monoolefinic acrylic acids of the structure

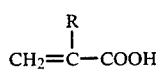

where R is a substituent selected from the group consisting of hydrogen and lower alkyl groups; most preferred is acrylic acid.

Preferred carboxyvinyl polymers used in formulations of the present invention have a molecular weight of at least about 750,000; more preferred are carboxyvinyl polymers having a molecular weight of at least about 1,250,000; most preferred are carboxyvinyl polymers having a molecular weight of at least about 3,000,000. Mixtures of carboxyvinyl polymers may also be used herein.

Various carboxyvinyl polymers are commercially available from B. F. Goodrich Company, New York, N.Y., under the tradename Carbopol. Carboxyvinyl polymers found useful in the formulations of the present invention include Carbopol 910 having a molecular weight of about 750,000, preferred Carbopol 941 having a molecular weight of about 1,250,000, and highly preferred Carbopols 934 and 940 having molecular weights of about 3,000,000 and 4,000,000 repectively.

Highly preferred Carbopol 940 is a very slightly cross-linked carboxyvinyl polymer having a molecular weight of about 4,000,000. It has been described as a high molecular weight polyacrylic acid cross-linked with about 1% of polyallyl sucrose having an average of about 5.8 allyl groups for each molecule of sucrose.

The carboxyvinyl polymer is used in the present compositions at a level of from about 0.01% to about 0.8% preferably from about 0.1% to about 0.5%

The polymer is present in an amount such that the carrageenan:carboxyvinyl polymer ratio is from about 100:1 to about 1.2:1 preferably from about 5:1 to about 1.5:1.

CARRAGEENAN

The carrageenan used in the compositions of the present invention is the iota form. Lota from carageenan, like the other carrageenans, contains repeating galactose units (sulfated or non-sulfated) joined by 1–3, 1–4 glycosidic linkages. Iota form is thought to contain about 30% 3,6 anhydro-D-galactose and about 32% ester sulfate by weight. This material is an item of commerce and can be obtained from Hercules Chemical Company under the tradename Genuvisco Type 0819. Another source of supply is the Marine Colloids Division of the FMC Corporation. The molecular weight of the carrageenan will normally be in the range of from about 5,000 to about 500,000, preferably from about 100,000 to about 500,000. The carrageenan is preferably used in salt form, most preferably when fluoride is in the composition, as the sodium salt.

The amount of carrageenan in the compositions of the present invention is from about 0.1% to about 1.7%, preferably from about 0.25% to about 0.75%.

HUMECTANT

Another essential component of the toothpaste compositions herein is a humectant. The humectant serves to keep the toothpaste compositions from hardening upon exposure to air. Certain humectants can also impart desirable sweetness or flavor to toothpaste compositions. The humectant, on a pure humectant basis, generally comprises from about 20% to 70%, preferably from about 30% to 65%, by weight of the toothpaste compositions herein.

Suitable humectants for use in this invention include edible polyhydric alcohols such as glycerine, sorbitol, xylitol, propylene glycol as well as other polyols and mixtures of these humectants. Sorbitol is frequently employed as a 70% aqueous solution known as Sorbo ®. Mixtures of glycerine and sorbitol are especially preferred as the humectant component of the toothpaste compositions herein.

WATER

Water is the last essential element of the toothpastes of this invention and forms the remainder of the compositions. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with Sorbitol.

OPTIONAL INGREDIENTS

In addition to the above described essential components, the toothpastes of this invention can contain a variety of optional conventional toothpaste ingredients. Such optional ingredients include for example fluoride ion sources, sudsing agents, flavoring agents, sweetening agents, anticalculus agents, antiplaque agents and coloring agents.

A preferred optional ingredient in the instant compositions is a fluoride ion source at a level of from about 0.01% to 3%, preferaoly from about 0.03% to 1.0%, by weight of the compositions. Such fluoride ions combine with dental enamel and thereby reduce enamel solubility in acid. Application of fluoride ions to dental enamel serves to protect teeth against decay.

A wide variety of fluoride ion-yielding materials can be employed as sources of soluble fluoride in the instant compositions. Examples of suitable fluoride ion-yielding materials are found in Briner et al, U.S. Pat. No. 3,535,421, issued Oct. 20, 1970; and Widder et al, U.S. Pat. No. 3,678,154, issued July 18, 1972, both patents being incorporated herein by reference. Preferred fluoride ion sources for use herein include sodium fluoride, stannous fluoride, potassium fluoride, potassium stannous fluoride ($SNF_2$—KF), indium fluoride, zinc fluoride, ammonium fluoride and stannous chlorofluoride. Stannous fluoride and sodium fluoride are particularly preferred, as well as mixtures thereof.

Another anticaries agent suitable for use in the present compositions is sodium monofluorophosphate. This agent can be used alone or in combination with one or more of the above described materials.

Preferably the instant toothpaste compositions provide from about 50 ppm to 10,000 ppm, more preferably from about 100 to 3000 ppm, of fluoride ions in the aqueous solutions which contact dental surfaces when the toothpastes of the present invention are used in the mouth. Such solutions are simulated by preparing 3:1 water/toothpaste slurries (by weight) of the toothpaste compositions herein and by subsequently centrifuging such slurries to obtain an aqueous supernatant. The fluoride ion concentration in such a supernatant is taken as a measure of the "soluble fluoride" provided by any given fluoride toothpaste composition.

Another preferred optional ingredient is a sudsing agent. Suitable sudsing agents are those which are reasonable stable and form suds throughout a wide pH range, i.e., non-soap anionic, nonionic, cationic, zwitterionic and amphoteric organic synthetic detergents. Sudsing agents of these types are described more fully in Agricola et al, U.S. Pat. No. 3,959,458, May 25, 1976 and in Haefele, U.S. Pat. No. 3,937,807, Feb. 10, 1976. Both of these patents are incorporated herein by reference.

Anionic sudsing agents useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixture of anionic surfactants can also be employed.

The nonionic sudsing agents which can be used in the toothpastes of the present invention can be broadly defined as compounds produced by the condensation of alkylene oxide groups (hydrophilic in nature) with an organic hydrophobic compound which may be aliphatic or alklaromatic in nature. Examples of suitable nonionic sudsing agents include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

The zwitterionic synthetic sudsing agents useful in the toothpastes of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains as anionic water-solubilizing group, e.g., carboxy, sulfonate, sulfate, phosphate, or phosphonate.

The cationic sudsing agents useful in the toothpastes of the present invention can be broadly defined as quaternary ammonium compounds having one long alkyl chain containing from about 8 to about 18 carbon atoms such as lauryl trimethylammonium chloride; cetyl pyridinium chloride; cetyl trimethylammonium bromide; di-isobutylphenoxyethoxyethyl-dimethylbenzylammonium chloride; coconutalkyltrimethylammonium nitrite; cetyl pyridinium fluoride; etc. Especially preferred are the quarternary ammonium fluorides described in U.S. Pat. No. 3,535,421, Briner et al, Oct. 20, 1970, incorporated by reference hereinbefore, where said quarternary ammonium fluorides have detergent properties. The cationic sudsing agents can also act as germicides in certain of the toothpastes herein.

The amphoteric agents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water-solubilizing group, e.g., carboxylate, sulfonate, sulfate, phosphate, or phosphonate.

The sudsing agent can be present in the toothpaste compositions of this invention in an amount from 0.1% to 6% by weight of the total composition.

Flavoring agents can also be added to the instant compositions. Suitable flavoring agents include oil of wintergreen, oil of peppermint, oil of spearmint, oil of sassafras, and oil of clove. Sweetening agents which can be used include saccharin, dextrose, levulose, aspartame, D-tryptopnan, dihydrochalcones, acesulfame and sodium cyclamate. Flavoring agents are generally used in toothpastes at levels of from about 0.01% to 2% by weight and sweetening agents at levels from about 0.05% to about 2% by weight.

Phosphorus-containing anticalculus agents and/or bisbiguanide antiplaque agents can also optionally be added to the toothpastes of this invention. Phosphorus-containing anticalculus agents such as disodium ethane-1-hydroxy-1, 1-diphosphonate and related materials are described more fully in McCune et al, U.S. Pat. No. 3,488,419, issued Jan. 6, 1970, incorporated herein by reference. Bis-biguanide antiplaque agents such as chorhexidine (1,6-bis[$N^5$-p-chlorophenyl-$N^1$-biguanido]-hexane), the soluble and insoluble salts thereof and related materials such as 1,2-bis-($N^5$-p-tri-fluoromethyl-phenyl-$N^1$-biguanido)ethane are described more fully in Haefele, U.S. Pat. No. 3,934,002, Jan. 20, 1976; Haefele, U.S. Pat. No. 3,937,807, Feb. 10, 1976; Procter & Gamble, Belgian Pat. No. 843,244, published Dec. 22, 1976 and Procter & Gamble, Belgian Pat. No. 844,764, published Jan. 31, 1977. These patents are incorporated herein by reference.

If present, the optional anticalculus and/or antiplaque agents generally comprise from about 0.01% to 2.5% by weight of the toothpaste compositions herein.

METHOD OF MANUFACTURE

Toothpaste compositions of the present invention are prepared using reasonably conventional toothpaste preparation techniques. For example, part of the humectant and the dental abrasive may be mixed together with a sweetener, a buffering agent and an opacifier (if these materials are present) to form one mixture. Some water and a fluoride source may be mixed together to form a solution which is added to the abrasive slurry. The carboxyvinyl polymer and the carrageenan may then be mixed The carboxyvinyl polymer and the carrageenan may then be mixed slowly through a screen to minimize lumping with part of the humectant to form a gel slurry. The slurry is then milled prior to being added to the other toothpaste components. A suitable mill is a Tri blender offered by Ladish Company.

Once prepared, the compositions herein provide a pH of from about 6.0 to 8.0, preferably 6.8 to 8.0; when said compositions are slurred with water in a 3:1 weight ratio of water to composition. Fluoride toothpastes providing pH values within the 6.8 to 8.0 range provide especially stable fluoride stability compared to toothpastes with pH values outside this range. Flavoring of toothpastes within this pH range is also comparatively easy.

COMPOSITION USE

Toothpaste compositions of the present invention are used in conventional manner. The toothpaste compositions or slurries thereof are brushed onto dental surfaces and subsequently rinsed away.

During use of the toothpaste herein in conventional manner, pastes or slurries generally contact dental surfaces for at least about 30 seconds. More preferably such pastes or slurries contact dental surfaces for at least about 60 seconds.

Several representative toothpastes of the present invention are set forth in the following examples. All percentages used herein are by weight unless otherwise designated.

EXAMPLE I

The following is a representative toothpaste of the present invention.

| Component | Wt % |
| --- | --- |
| Sorbitol (70% Concentration) | 42.361 |
| Precipitated Silica[1] | 24.500 |
| Flavor | 0.930 |
| Saccharin | 0.133 |
| Sodium Fluoride | 0.243 |
| Sodium Alkyl Sulfate (28% concentration) | 4.000 |
| Monosodium Phosphate | 0.470 |
| Trisodium Phosphate | 1.570 |
| Carbopol 940[2] | 0.250 |
| Carrageenan[3] | 0.500 |
| Water | 24.793 |
| Preservative | 0.200 |
| Dye | 0.050 |
| | 100.000 |

[1]Supplied by J. M. Huber as Zeodent 119
[2]Supplied by B. F. Goodrich Carboxyvinyl polymer
[3]Iota from Carrageenan offered by Hercules Chemical Company This composition possesses good consistency, standup and handling characteristics.

EXAMPLE II

The following is another toothpaste representative of the present invention.

| Component | Wt % |
| --- | --- |
| Sorbitol (70% Concentration) | 53.361 |
| Precipitated Silica | 15.000 |
| Flavor | 0.600 |
| Sweetener | 0.320 |
| Sodium Fluoride | 0.243 |
| Sodium Alkyl Sulfate (28% concentration) | 4.000 |
| Preservative | 0.200 |
| Monosodium Phosphate | 0.590 |
| Trisodium Phosphate | 1.450 |
| Carbopol 940 | 0.300 |
| Carrageenan | 0.600 |
| Water | 23.311 |
| Dye | 0.025 |
| | 100.000 |

EXAMPLE III

The following is a toothpaste representative of the present invention.

| Component | Wt % |
| --- | --- |
| Sorbitol (70% Concentration) | 60.197 |
| Precipitated Silica | 20.000 |
| Flavor | 0.900 |
| Saccharin | 0.133 |
| Sodium Fluoride | 0.243 |
| Sodium Alkyl Sulfate (28% concentration) | 4.000 |
| Monosodium Phosphate | 0.590 |
| Trisodium Phosphate | 1.450 |
| Carbopol 940 | 0.200 |
| Carrageenan | 0.400 |
| Water | 11.837 |
| Dye | 0.050 |
| | 100.000 |

EXAMPLE IV

| Component | Wt % |
| --- | --- |
| Sorbitol (70% Concentration) | 42.361 |
| Silica B-30-P[1] | 30.000 |
| Flavor | 0.960 |
| Saccharin | 0.140 |
| Sodium Fluoride | 0.243 |
| Titanium Dioxide | 0.450 |
| Sodium Alkyl Sulfate | 4.000 |
| Preservative | 0.200 |
| Trisodium Phosphate | 1.570 |
| Monosodium Phosphate | 0.470 |
| Carbopol 940 | 0.250 |
| Carrageenan | 0.500 |
| Water | 18.806 |
| Dye | 0.050 |
| | 100.000 |

[1]Silica gel provided by Davison Chemical Division of W. R. Grace & Company

Examples II–IV perform in the manner indicated above for Example I.

In the above compositions the abrasive may be replaced by other abrasives such as calcium carbonate, calcium pyrophosphate, tricalcium phosphate, dicalcium othophosphate dihydrate and hydrated alumina with similar results obtained. Similarly other carboxyvinyl polymers such as Carbopol 934 and 941 may be used as well as other fluoride sources such as stannous fluoride, potassium fluoride, indium fluoride, zinc fluoride and sodium monofluorophosphate. Silicas are the preferred abrasives when fluoride sources are used in the compositions.

What is claimed is:

1. A toothpaste composition comprising:

a. from about 6% to about 35% of a silica dental abrasive;
b. from about 20% to about 70% of a humectant;
c. from about 0.01% to about 0.8% of a carboxyvinyl polymer;
d. from about 0.1% to about 1.7% of an iota form carrageenan; and
e. q.s. 100% water;

said composition providing a pH of from about 6.0 to about 8.0 when slurried with water in a 3:1 water:-composition weight ratio and the weight ratio of carrageenan:carboxyvinyl polymer is from about 100:1 to about 1.2:1.

2. A toothpaste composition according to claim 1 wherein the amount of abrasive is from about 15% to about 25% and the amount of humectant is from about 30% to about 65%.

3. A toothpaste composition according to claim 2 wherein the amount of carboxyvinyl polymer is from about 0.1% to about 0.5% and the amount of carrageenan is from about 0.25% to about 0.75%.

4. A toothpaste composition according to claim 3 wherein the humectant is selected from the group consisting of sorbitol, glycerine and mixtures thereof.

5. A toothpaste composition according to claim 1 wherein and the composition also contains a soluble fluoride source.

6. A toothpaste composition according to claim 5 wherein the soluble fluoride source is selected from the group consisting of sodium fluoride, stannous fluoride and mixtures thereof.

7. A toothpaste composition according to claim 6 wherein the amount of carboxyvinyl polymer is from about 0.1% to about 0.5% and the amount of carrageenan is from about 0.25% to about 0.75%.

8. A toothpaste composition according to claim 7 wherein the silica abrasive is a precipitated silica.

9. A toothpaste composition according to claim 8 wherein the soluble fluoride source is sodium fluoride.

10. A toothpaste composition according to claim 1 which also contains an anti-calculus agent.

* * * * *